(12) United States Patent
Sulmon et al.

(10) Patent No.: US 8,222,187 B2
(45) Date of Patent: Jul. 17, 2012

(54) METHOD FOR IMPROVING THE PHYTOREMEDIATION OF POLLUTED SITES BY PROVIDING PLANTS WITH EXOGENOUS CARBOHYDRATES

(75) Inventors: Cecile Sulmon, Villepinte (FR); Gwenola Gouesbet, Rennes (FR); Ivan Couee, Rennes (FR); Abdelhak El Amrani, Rennes (FR)

(73) Assignee: Universite de Rennes 1, Rennes Cedex (FR)

( * ) Notice: Subject to any disclaimer, the term of this patent is extended or adjusted under 35 U.S.C. 154(b) by 1291 days.

(21) Appl. No.: 10/571,522

(22) PCT Filed: Sep. 9, 2004

(86) PCT No.: PCT/FR2004/002294
§ 371 (c)(1),
(2), (4) Date: Jan. 5, 2007

(87) PCT Pub. No.: WO2005/025769
PCT Pub. Date: Mar. 24, 2005

(65) Prior Publication Data
US 2007/0093388 A1 Apr. 26, 2007

(30) Foreign Application Priority Data
Sep. 12, 2003 (FR) .................................... 03 10774

(51) Int. Cl.
*A01N 25/26* (2006.01)
*A01N 63/00* (2006.01)
*A01N 35/00* (2006.01)
*A01N 31/00* (2006.01)

(52) U.S. Cl. ........ 504/100; 504/118; 504/348; 504/351; 504/353

(58) Field of Classification Search .................. None
See application file for complete search history.

(56) References Cited

U.S. PATENT DOCUMENTS

| 4,291,497 A | 9/1981 | Manankov | ........................ 47/58 |
| 2003/0162664 A1 | 8/2003 | Walker | ........................ 504/367 |

FOREIGN PATENT DOCUMENTS

| EP | 1260282 | * | 11/2002 |
| JP | 05239458 | * | 3/1992 |
| JP | 2000106777 | * | 4/2000 |
| WO | WO 96/32016 | | 10/1996 |
| WO | WO 97/34714 | | 9/1997 |
| WO | WO-9734714 | * | 9/1997 |

OTHER PUBLICATIONS

An et al., "Phyto-remediation of DDT and its Main Degradation Product-Contaminated Soils using Grasses," CA, 2003, XP002272267, pp. 1.
European Search Report for corresponding European Application No. 03 10774, filed Sep. 12, 2003.

* cited by examiner

*Primary Examiner* — Alton Pryor
(74) *Attorney, Agent, or Firm* — David D. Brush; Westman, Champlin & Kelly, P.A.

(57) ABSTRACT

A method is provided for phytoremediating a site polluted by at least one type of pollutant, comprising at least one step comprising growing, on this polluted soil, at least one phytoremediating plant capable of fixing at least a portion of this pollutant, and comprising a subsequent step comprising of harvesting or destroying this plant that has fixed at least a portion of said pollutant. The step of growing the plant is effected, at least in part, in the presence of at least one water-soluble exogenous carbohydrate that can be assimilated by the plant or in the presence of a substance containing a carbohydrate of this type.

16 Claims, 6 Drawing Sheets

Soil with atrazine contamination corresponding to diffuse pollution

Sucrose treatment    no treatment

METHOD FOR IMPROVING THE PHYTOREMEDIATION OF POLLUTED SITES BY PROVIDING PLANTS WITH EXOGENOUS CARBOHYDRATES

CROSS-REFERENCE TO RELATED APPLICATION

This application is a Section 371 National Stage Application of International Application No. PCT/FR2004/002294, filed Sep. 9, 2004 and published as WO 2005/025769 A1 on Mar. 24, 2005, not in English.

FIELD OF THE DISCLOSURE

Background of the Disclosure

This disclosure relates to the field of biological control against the pollution of natural or artificial sites.

More specifically, the disclosure relates to a phytoremediation method intended to significantly reduce the concentration, or ideally remove any presence, in a site, of pollutants generated by human, agricultural or industrial activities.

Although an embodiment of the invention can also be applied to the removal of hydrocarbons and certain heavy metals, including radionuclides, from polluted sites, it is more specifically applied to the removal or the reduction of herbicides and pesticides.

In particular, an embodiment of this invention is particularly useful for depolluting sites polluted with triazines, particularly atrazine, or with different classes of photosynthesis-inhibiting herbicides.

Triazines are herbicides that have been used abundantly in agriculture since the 1960s. They have in particular been widely used by conventional corn producers. An atrazine pollution of around 5 mg/L in interstitial water is normally observed in agriculture parcels.

Atrazine (2-chloro-4-ethylamino-6-isopropylamine-1,3, 5-triazine) is a molecule that inhibits photosynthesis (more specifically, photosystem II), i.e. the transformation of light energy into electrochemical energy, causing the formation of oxygen and chlorophyll radicals that lead to oxidative stress and membrane lipid peroxidation. The photosynthesis of the plant, and consequently its growth, are thus blocked.

Atrazine stays in water and is mobile in soil. This compound then moves into surface water by the dissolution of its pollution particles in rainwater. Therefore, it is not unusual to also find it in drinking water samples in some regions of France, such as Brittany, the Southwest or Île-de-France, at levels ten times higher than the threshold formerly authorised in France (0.1 mg/L).

Decades of use of triazines on agricultural soils have therefore left soils polluted, and it is now desirable to begin their decontamination. In addition, production, storage or accidental spill sites, with a high level of pollution, have multiplied.

Indeed, numerous studies have shown that the impact of atrazine on the environment and in particular on wildlife was very disturbing. Alarming abnormalities have thus been found in some amphibians in the United States.

Atrazine is also strongly suspected to have harmful effects on humans, as it appears to cause stomach cancers in particular.

A number of countries have therefore decided to limit or prohibit the use of this compound. Thus, in France, the use of atrazine in the agricultural environment has been prohibited since 30 Jun. 2003. Atrazine however remains the most commonly used pesticide in the United States and in many developing countries.

More specifically with regard to triazines, it is known that some plants have become naturally resistant to these compounds. This resistance most often results from a natural genetic mutation of the psbA gene which encodes the D1 protein (to which atrazine binds so as to disrupt and then block the photosynthesis of the plant). This mutation leads to a modification of the binding site of the D1 protein with atrazine, leading to resistance.

The resistance to atrazine may also result from a biochemical adaptation of the plant. Thus, by increasing the glutathione-s-transferase activities, sorghum can "immunise" itself against atrazine.

The prior art has proposed transgenic plants in which a gene of bacterial origin has been introduced, which enables an atrazine degradation system to be integrated into said plants. However, such plants constitute genetically modified organisms, which currently do not have the favour of public opinion.

The prior art also discloses methods for phytoremediation of polluted sites. Such methods consist of cultivating, on the sites, polluted phytoremediation plants that, as they grow, absorb all or some of the pollution contained at these sites into their tissue.

Thus, the technique described in the international patent application WO 96/32016 consists of using plants of the Brassicaceae family in the presence of bacteria of the *Pseudomonas* and *Bacillus* genus to absorb certain heavy metals contained in polluted soils. These micro-organisms are introduced to the plant roots, the plants themselves, their seeds or the soil in which the plants grow. The use of such bacteria is relatively complex to implement, in particular due to the competition with other bacteria present in the plant culture site.

In any case, such methods are limited with regard to the absorption of substances that are harmful to the plants, such as herbicides.

SUMMARY

An embodiment of the invention relates to a method for phytoremediation of a polluted site by at least one type of pollutant, which method includes at least one step comprises cultivating, on said polluted site, at least one phytoremediation plant capable of absorbing at least some of said pollutant and a subsequent step comprising collecting or destroying said plant that has absorbed at least some of said pollutant, wherein said step comprises cultivating said plant is performed at least partially in the presence of at least one water-soluble exogenous carbohydrate that can be absorbed by said plant, or a substance containing such a carbohydrate.

Thus, the method of an embodiment of the invention proposes an original way in which to cultivate the phytoremediation plant directly in the site to be depolluted in the presence, during all or part of the culture cycle, of at least one water-soluble exogenous carbohydrate that can be absorbed by this plant.

The inventors have indeed observed that, surprisingly, the presence of such a sugar enabled the phytoremediation plants to be made resistant to pollutant concentrations that were hundreds of times higher than in the absence of sugar.

It should be noted that, in the context one or more embodiments of this invention, it is possible to use such a sugar absorbable by the plant alone or in a mixture with other sugars. This sugar or this mixture of sugars can also be included in one of the substances containing them, as will be described below.

There are many water-soluble carbohydrates that can be absorbed by plants. Depending on the phytoremediation plant selected, according to the type of pollution of the site to be treated, the nature of this exogenous carbohydrate can vary.

However, it is preferably a monosaccharide, a disaccharide or a trisaccharide.

Thus, according to an alternative embodiment of the invention, it can be glucose.

According to one preferred alternative, among others, this exogenous sugar comprises sucrose. Indeed, this carbohydrate corresponds to the primary form of transport of sugars into plants and distribution in the plant tissue.

As already indicated, the method according to an embodiment of the invention can be implemented so as to treat various types of pollutants (hydrocarbons, certain heavy metals, herbicides, pesticides, and so on).

The method according to an embodiment of the invention is particularly suitable for the treatment of organic or metallic pollutants that cause oxidative stress that indirectly inhibits photosynthesis, and in particular photosynthesis-inhibiting herbicides.

However, this pollutant is preferably a herbicide belonging to the triazine family, or more generally a photosynthesis-inhibiting herbicide. The method will thus preferably be used to depollute sites polluted by atrazine.

According to an advantageous alternative embodiment of the invention, the carbohydrate used can be in the form of a substance containing it. Thus, it can be an industrial residue such as, for example, molasses from the sugar industry.

Various means for introducing such an exogenous carbohydrate to the phytoremediation plant can be envisaged.

According to one embodiment, it is possible to consider coating the seeds of this plant with the carbohydrate. Such a coating can be performed extemporaneously to the culture, for example, by a seed dealer. Such coated grains have the advantage of being capable of being used with great flexibility without requiring subsequent intervention on the culture medium.

However, according to another embodiment, it is also possible to consider introducing the carbohydrate or the substance containing it to the site or integrating it into the soil. In this case, the exogenous carbohydrate or the substance containing it can be introduced in solid form or in liquid form in a solution.

The amount and concentration of such a sugar introduced to the phytoremediation plant will be based on numerous factors, in particular the nature of the pollutants present at the site, the concentration of said pollutants, the type of phytoremediation plant, the density of phytoremediation plants, the tolerance of said plant for said sugar, the brightness and the micro-climatic conditions, the nitrogen content of the site treated, the physicochemical nature of the site, and the structure of the soil.

By way of indication, it is possible to use a treatment of 50 grams to 500 grams of carbohydrates per meter squared.

By way of indication, it is also possible to water the phytoremediation plants with a solution of 2 to 60 grams per liter of sucrose equivalent in the case of soil, and if it is an inundated site, it is possible to adjust the water of the site to a final concentration of 2 to 60 grams per liter of sucrose equivalent.

It should also be noted that the exogenous carbohydrate can be introduced to the site before starting the culture, as well as after the culture has begun, for example, when the seedlings have begun to grow or both at the beginning and during the culture at one or more times.

It should also be noted that the carbohydrate can be introduced to a native vegetation cover pre-existing at the site.

The phytoremediation plant used can vary according to the type of pollution and in particular its concentration.

Thus, for sites with deep pollution, it is possible to choose a plant with deep root growth, such as a tree and in particular poplars.

In the case of very moist sites or sites containing pollutant-laden waters, it is possible to use aquatic plants such as, for example, water reeds.

By contrast, for relatively unpolluted sites, it is possible to consider using plants that grow quickly and in particular annual or biannual plants. A plurality of growth cycles and mowing of the plants can be envisaged.

Among these, clover, ryegrass, *Arabidopsis thaliana* and plants of the crucifer family (Brassicaceae) and in particular mustards and species of the *Brassica* genus can notably be cited.

It should be noted that *Arabidopsis thaliana* serves as a plant model in genetics and molecular biology. It is a small crucifer related to wild mustard that is very common in temperate regions and that has the advantage of being a non-agricultural plant not picked by humans. It is therefore used as a wild plant model and various studies that have been conducted on it have made it possible to demonstrate that it has mechanisms for protection against triazines and in particular against atrazine, which are dependent on the presence of sucrose.

One or more embodiments of the invention, as well as the various advantages that it may have, can be better understood from the following description, provided with reference to the figures.

DETAILED DESCRIPTION OF ILLUSTRATIVE EMBODIMENTS

The inventors successfully conducted a number of experiments enabling it to be proved that the addition of water-soluble exogenous carbohydrates to the culture medium of the *Arabidopsis thaliana* plant gave the latter increased tolerance for atrazine, even at high concentrations. In this context, sucrose and glucose were tested.

*Arabidopsis thaliana* seeds (Wassilewskija ecotype) were sterilised at the surface according to the standard protocol and then rinsed with absolute ethanol and dried for one night.

These seeds were cultivated in Petri dishes on a culture medium of Murashige and Skoog (adjusted to a pH of 5.7) containing agar (0.8%). The Petri dishes were stored for 48 h at 4° C. then transferred to 22° C. under a photoperiod of 16 hours per day at 4500 lux. The sucrose and glucose were added to the culture medium, while no sugar was added for the controls.

A growth parameter (length of the primary roots) and the pigment levels (chlorophylls and carotenoids) were measured after 15 days of culture. The atrazine levels in the plants were also measured after one month of culture.

The photosynthetic pigments (chlorophylls and carotenoids) were extracted by grinding the aerial portions of the plants in 80% acetone and by measuring the absorbance of the extracts corresponding to 663 nm, 646 nm and 470 nm. The levels of these pigments were expressed in µg/mL and determined according to the method of Lichtenthaler et al. (1983 Biochem. Soc. Trans. 11, 591-592).

Figure 1:
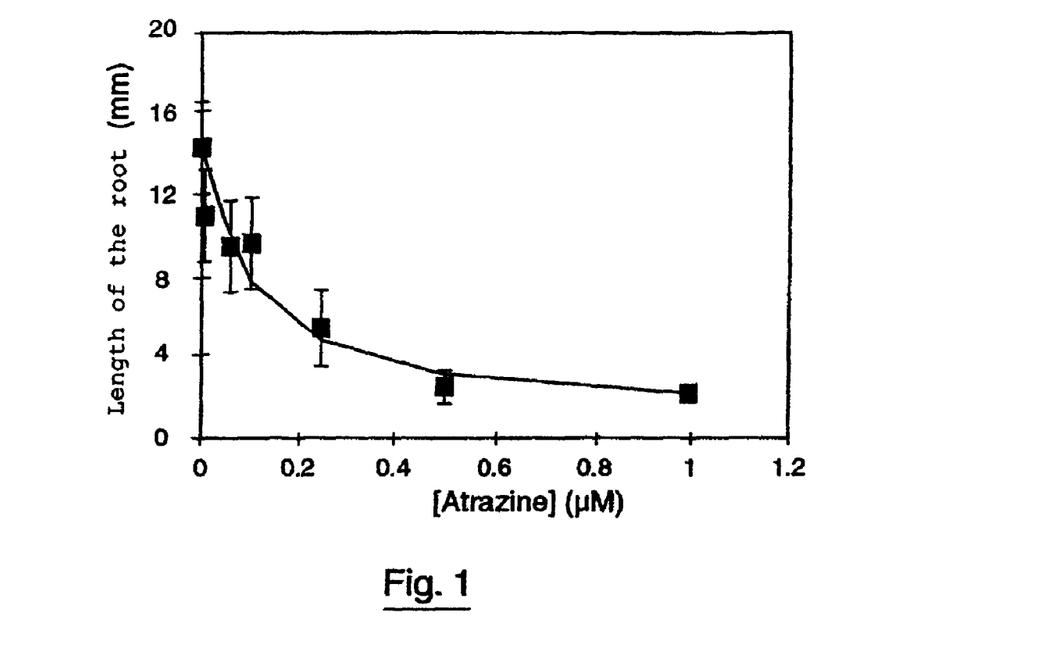
FIG. 1 shows the effect of increasing atrazine levels in a culture medium on the length of the primary roots of *Arabidopsis thaliana*.

FIG. 1 shows the results obtained for the lengths of the primary roots in mm as a function of the atrazine concentrations tested, in the absence of sugars in the culture medium.

These results show that the effect of atrazine on the length of the *Arabidopsis thaliana* roots becomes significant at a concentration on the order of 100 nM to 250 nM. At 500 nM, the inhibition of root development is complete and causes discolouring and death of the plants.

These results clearly indicate that the growth inhibition caused by atrazine is dependent on the concentration of this compound, as shown by the hyperbolic regression curve ($R^2=0.93$) shown with a solid line in FIG. 1, which gives an $I_{50}$ of 120 nM for the atrazine inhibition.

Figure 2:
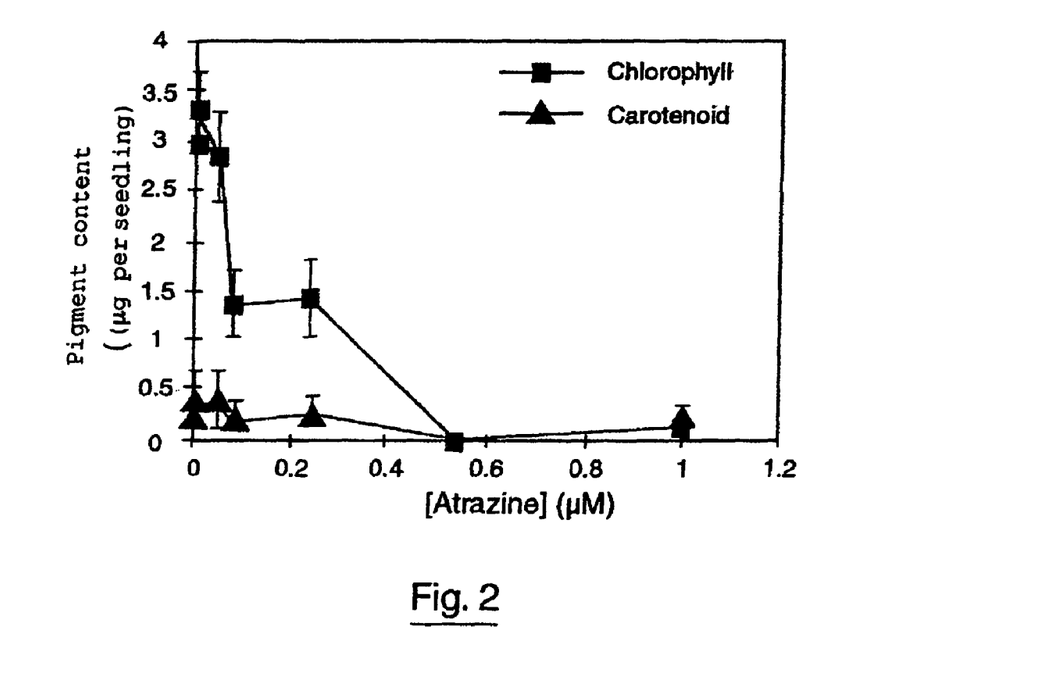
FIG. 2 shows the effect of increasing atrazine levels in a culture medium on the concentration of photosynthetic pigments (chlorophylls and carotenoids) in *Arabidopsis thaliana*.

FIG. 2 shows the results obtained for the levels of chlorophylls and carotenoids, in the absence of sugars in the culture medium.

These results show that the chlorophyll levels begin to diminish for an atrazine concentration between 50 and 100 nM, with the chlorophylls and carotenoids disappearing completely at a concentration of 500 nM.

Figure 3:
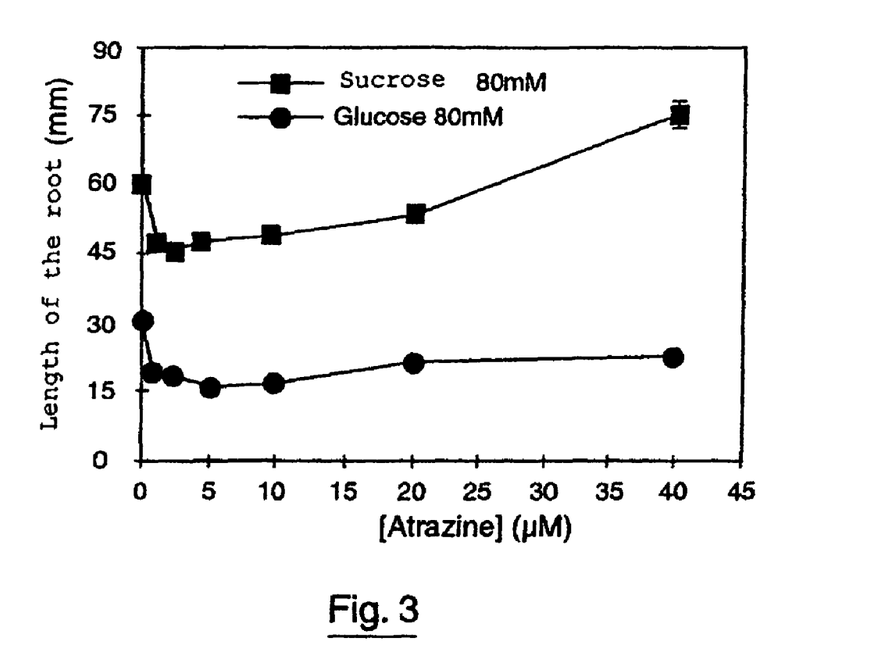
FIG. 3 shows the effect of increasing atrazine levels in a culture medium on the length of the primary roots of *Arabidopsis thaliana* in the presence of sucrose or glucose.

FIG. 3 shows the results obtained for the length of the primary roots as a function of the atrazine content of the medium in the presence of 80 mM of sucrose or 80 mM of glucose.

These results show that levels from 1 to 10 µM of atrazine have an inhibiting but non-lethal effect on the length of the primary roots, but that higher atrazine concentrations paradoxically enable the root growth to improve.

This increase in growth is greater in the presence of sucrose than in the presence of glucose.

Figure 4:
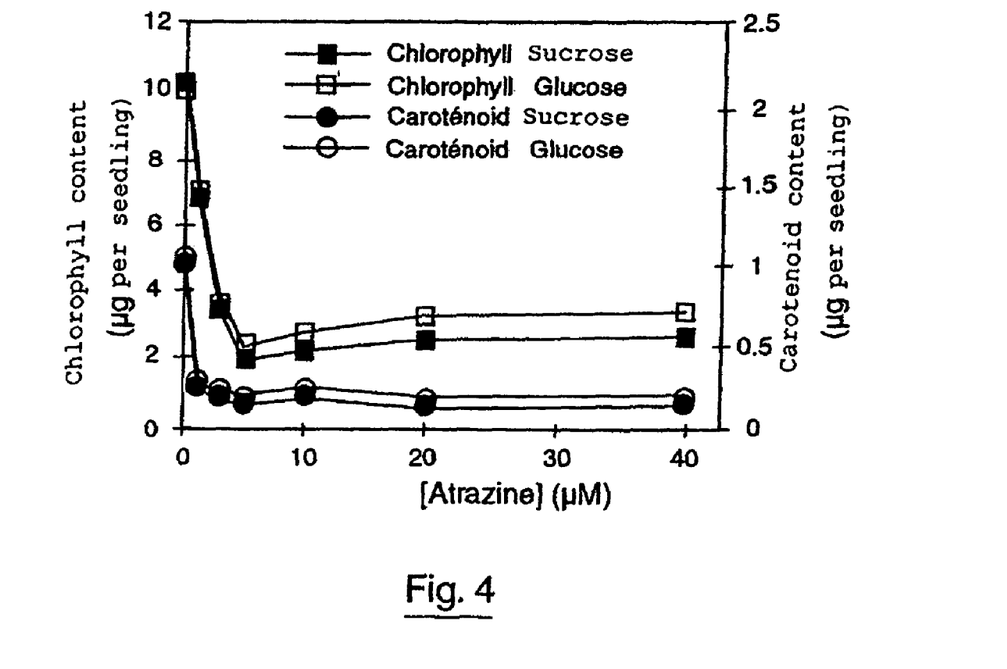
FIG. 4 shows the effect of increasing atrazine levels in a culture medium on the concentration of photosynthetic pigments (chlorophylls and carotenoids) in *Arabidopsis thaliana* in the presence of sucrose or glucose.

FIG. 4 shows the results obtained for photosynthetic pigment levels (chlorophyll and carotenoid levels) in the presence of 80 mM of sucrose or 80 mM of glucose.

These results indicate that if the atrazine causes a reduction in the levels of chlorophylls and carotenoids in the leaves in the presence of glucose and sucrose, the production of these pigments is not suppressed, while it is in the absence of sugar (see FIG. 2).

In another experiment series, *Arabidopsis thaliana* plants were cultivated in the culture medium described above in the absence of sucrose and in the presence of 10 mM and 80 mM of sucrose, and in the absence of atrazine and in the presence of 0.25 µM and 1 µM of atrazine.

Figure 5:
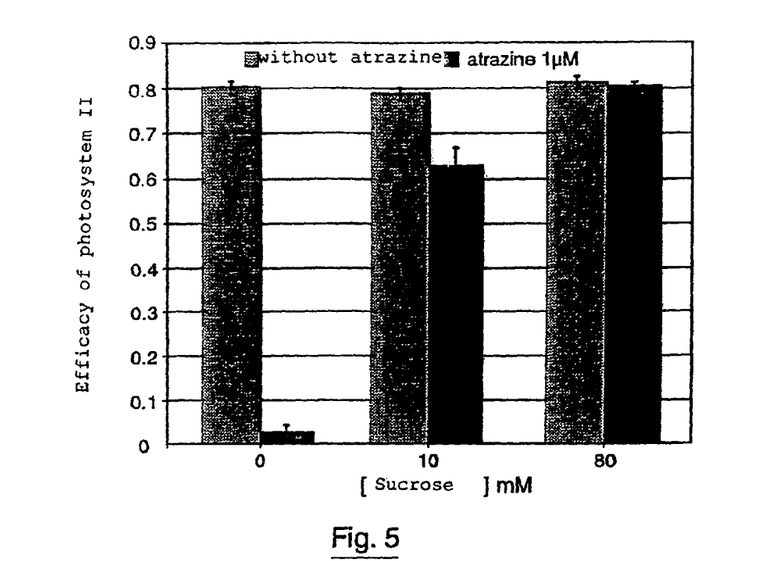
FIG. 5 shows effect of increasing sucrose levels on the efficacy of photosystem II, in the absence and in the presence of atrazine.

The results shown in FIG. 5 shows that increasing concentrations of sucrose contribute to maintaining the activity of photosystem II in the presence of atrazine doses that are lethal or sublethal in the absence of sucrose. The activity of photosystem II is monitored by measuring the fluorescence of the chlorophylls.

To measure the levels of D1 protein (31-kD monomer and 21.5-kD by-products), the membrane proteins of the plants were isolated according to the method of Pilgrim et al. (1998 Plant. J. 13 2-77-186). The levels of the total concentration of the target protein, D1 protein of photosystem II, were measured by Dot Blot analysis. Then, the different forms were analysed by gel electrophoresis separation under denaturing and Western Blot conditions.

Figure 7:
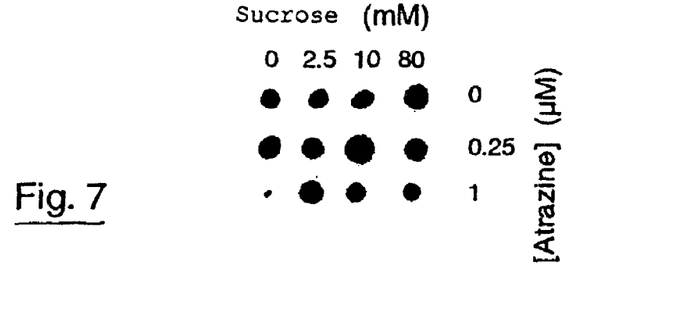
FIG. 7 shows a Dot Blot demonstrating the variation in level of all of the forms of the atrazine target protein (D1 protein of photosystem II) in the presence of increasing atrazine levels and different sucrose concentrations.

FIG. 7 shows the results obtained by Dot Blot, which detects all D1 proteins. According to this figure, it can be noted that 1 µM of atrazine causes the disappearance of the D1 protein in plants that were not cultivated in the presence of sucrose.

Figure 8:
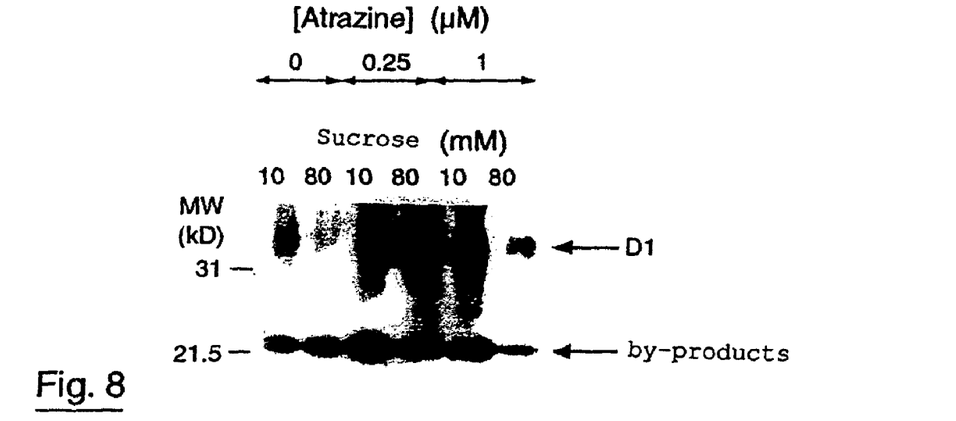
FIG. 8 shows a Western Blot demonstrating the variation in the target protein according to variable concentrations of atrazine and sucrose.

FIG. 8 shows the results obtained by Western Blot. These results show that high sucrose concentrations lead to a decrease in D1 protein production in the absence of atrazine, and that, by contrast, the presence of sucrose in the culture medium, and in the presence of 0.25 µM of atrazine, causes a greater accumulation of the D1 protein and its by-products. The same effect was observed with 1 µM of atrazine in the presence of 10 mM of sucrose. By contrast, the use of 80 mM of sucrose and 1 µM of atrazine causes a decrease in the D1 protein and by—products. The use of 80 mM of sucrose, however, makes it possible to maintain a sufficient amount of monomer of the D1 protein, which disappears at the same atrazine concentrations in the absence of sucrose.

In addition, the superoxide ion production of the plants was tested according to the method of Fryer et al. (2002 Imaging of photo-oxidative stress responses in leaves—J. Exp. Bot. 53: 1249-1254).

Figure 6:
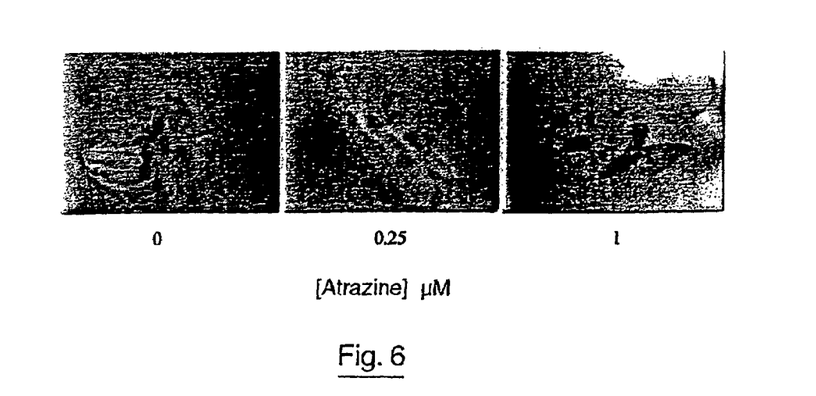
FIG. 6 shows the effect of increasing atrazine levels on the production of superoxide ion (responsible for oxidative stress) in the presence of 10 mM of sucrose.

As shown in FIG. 6, the presence of sucrose does not prevent the production of molecular species of active oxygen such as the superoxide ion which appears to increase in the presence of atrazine. The presence of sucrose does not block the action of atrazine and the production of superoxide ions, but protects the cells and the tissues from the destructive effects of oxidative stress.

Atrazine concentrations were also measured in the plants and the culture medium using conventional methods of extraction with solvents and high-performance liquid chromatography analysis with UV detection. The atrazine was extracted in a methanol and water mixture (4:1, v/v). After centrifugation, the supernatants were filtered on filters of 0.45 μm and the organic solvents were evaporated at 40° C. SPE cartridges were activated by washing with 5 mL or methanol then 5 mL of water. Each sample was applied to a column and the columns were then washed. The atrazine was eluted with 2 mL of dichloromethane. The organic solvents were then evaporated and the dry residues were dissolved in 500 μL of a methanol and water mixture (1:1). The samples were then analysed by HPLC with UV detection.

Figure 9:
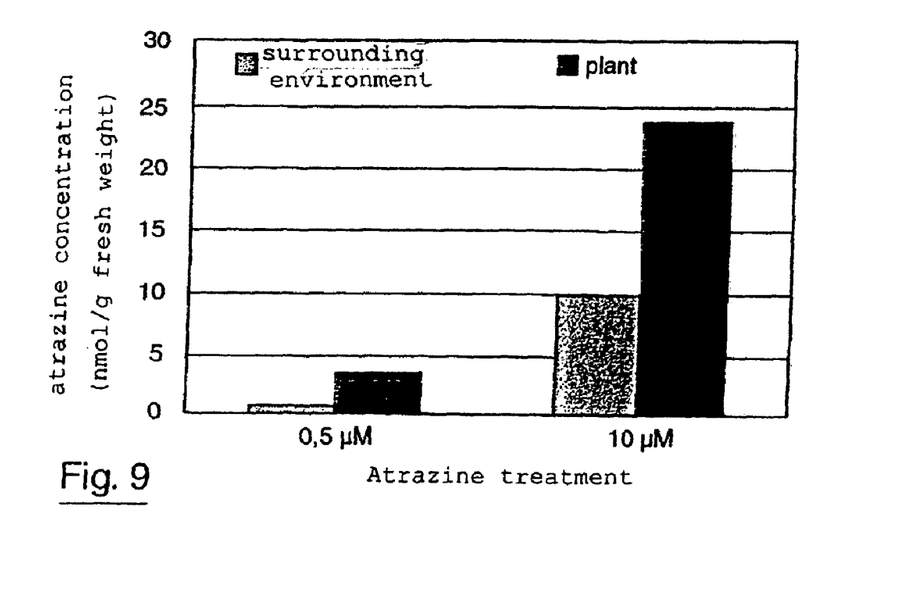
FIG. 9 shows the atrazine concentration in the plants as a function of the pollution of the surrounding environment.

As can be seen in FIG. 9, the plants cultivated in the presence of sucrose and in the presence of atrazine at 0.5 picomoles per milligram of medium have an atrazine content of 3.7 (±0.3) nanomoles of atrazine per gram of fresh weight. The atrazine is therefore at a higher concentration in the plant tissue than in the culture medium. In addition, plants treated with sucrose accumulate atrazine at a level that causes the death of plants in the absence of sucrose.

It appears that the tolerance to atrazine based on the use of sucrose, according to an embodiment of this invention, is not associated with a reduction in the atrazine level in tissues, but, on the contrary, to an over-accumulation of atrazine.

Figure 10:
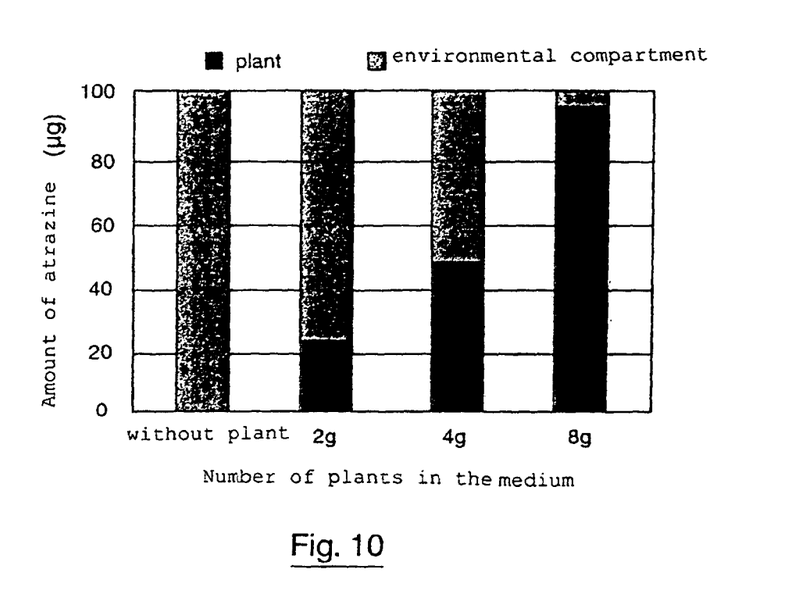
FIG. 10 shows the amounts of atrazine absorbed by *Arabidopsis* as a function of the number of seedlings introduced into the culture medium.

As shown in FIG. 10, the positive effects of sucrose on growth stimulation and the capacity to over-accumulate atrozine in the tissues mean that 8 g of fresh mass of *Arabidopsis* plants can accumulate 95 micrograms of atrazine from the surrounding agar medium.

Figure 11:
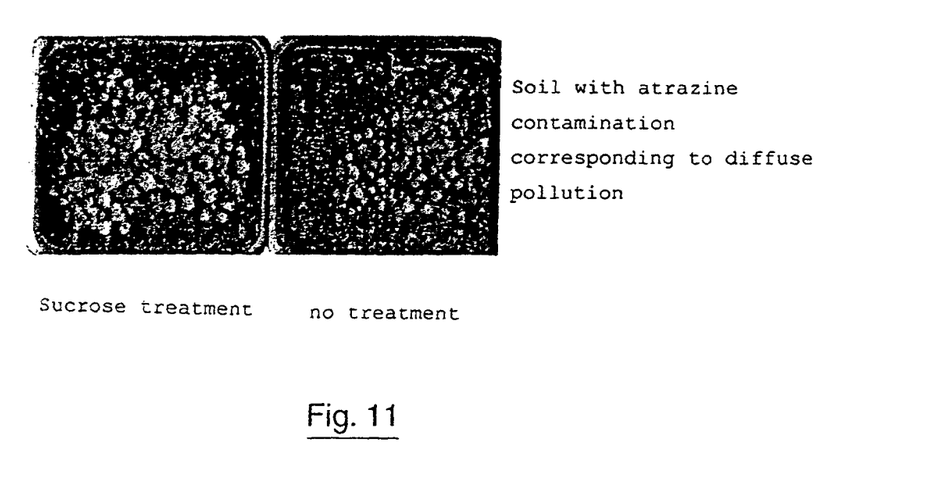
FIG. 11 shows, from above, two *Arabidopsis* cultures on humus having an atrazine contamination of 10 µM with or without the presence of sucrose.

In additional experiments, *Arabidopsis thaliana* was also cultivated on a humus contaminated at a concentration of 10 μM of atrazine in the absence of sucrose and in the presence of sucrose applied to the surface in the form of a 3% solution. The cultures obtained are shown in FIG. 11, in which the left-hand container corresponds to the culture in the presence of sucrose and the right-hand container corresponds to the culture in the absence of sucrose. The seedlings, clearly shown in this figure, are more numerous and larger when, according to an embodiment of the invention, sucrose has been added to the culture medium.

Figure 12:
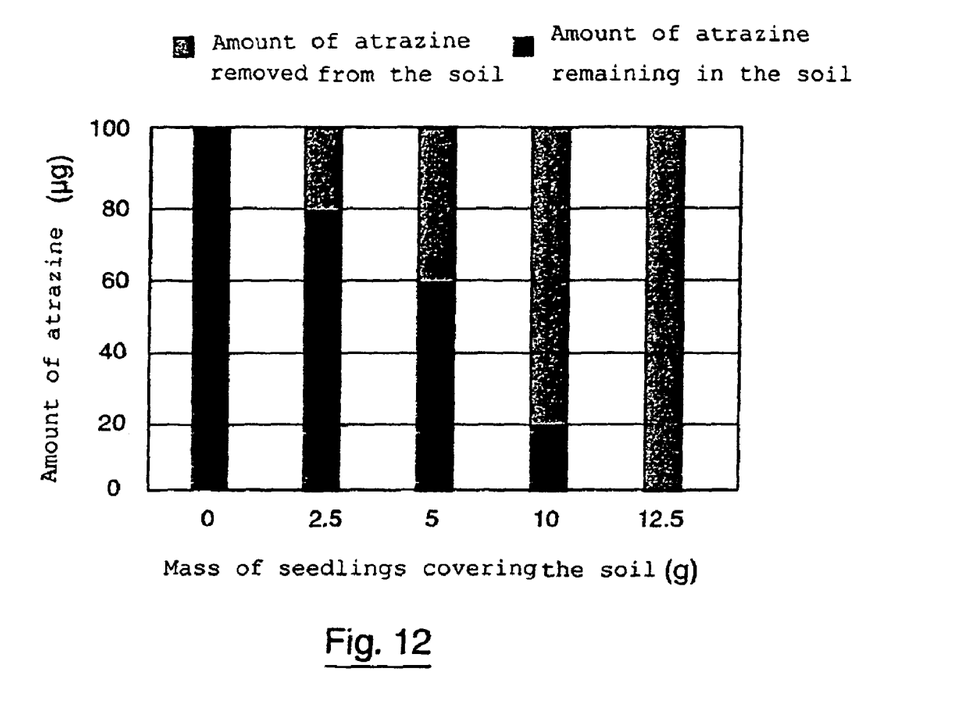
FIG. 12 shows the amounts of atrazine absorbed by *Arabidopsis* as a function of the number of seedlings cultivated on humus.

As shown in FIG. 12, the positive effects of sucrose on growth stimulation and the capacity to over-accumulate atrozine in the tissues mean that 12.5 g of fresh mass of *Arabidopsis* plants can accumulate 100 micrograms of atrazine from the surrounding humus medium.

These experiments showed that the use of a water-soluble exogenous carbohydrate during the culture of a phytoremediation plant gave this plant a greater tolerance for pollutants without inhibiting its growth, and enabling the pollutant to accumulate in said plant. The stimulation of growth, and therefore biomass, and the protection of the photosystems and cells against oxidative stress by introducing exogenous sugars indicate that an embodiment of the invention can be used to improve the accumulation, in phytoremediation plants tissues, of a wide range of organic and metallic pollutants other than herbicides.

An embodiment of the invention can therefore be used as an organic filter with various plant species with the goal, for example, of protecting sensitive sites. The use of carbohydrate, according to this embodiment, can be envisaged for the depollution of contaminated sites.

An embodiment of this invention proposes a new phytoremediation method that does not have the disadvantages of the prior art.

An embodiment of this invention proposes such a method that enables various types of organic and metallic pollutants to be accumulated in the plants with increased efficacy.

An embodiment of this invention also describes such a method that is inexpensive to implement.

The invention claimed is:

1. Method for phytoremediation of a site polluted by atrazine, which method comprising:
   at least one step comprising cultivating, on said polluted site, at least one phytoremediation plant, wherein said step of cultivating is performed in the presence of at least one water-soluble exogenous monosaccharide or disaccharide absorbable by said plant or a substance containing said monosaccharide or disaccharide wherein said monosaccharide or a disaccharide enhances the uptake or absorption of atrazine by said plant wherein the plant is resistant to the effects of greater concentrations of the atrazine relative to the same species of plant that was not cultivated in the presence of said monosaccharide or disaccharide, and wherein the monosaccharide or the disaccharide does not prevent the production of superoxide ion and does not block the action of atrazine in the plant; and
   a subsequent step comprising collecting or destroying said plant that has absorbed said atrazine.

2. Method according to claim 1, wherein said water-soluble exogenous monosaccharide comprises glucose.

3. Method according to claim 1, wherein said water-soluble exogenous disaccharide comprises sucrose.

4. Method according to claim 1, wherein said atrazine causes oxidative stress, which indirectly inhibits photosynthesis.

5. Method according to claim 1, wherein the substance containing said monosaccharide or disaccharide comprises an industrial residue.

6. Method according to claim 1, wherein said step comprising cultivating said plant in the presence of at least one water-soluble exogenous monosaccharide or disaccharide absorbable by said plant comprises using seeds of said plant coated with said monosaccharide or disaccharide.

7. Method according to claim 1, wherein said step comprising cultivating said plant in the presence of at least one water-soluble exogenous monosaccharide or disaccharide absorbable by said plant includes a step comprising introducing said monosaccharide or disaccharide or the substance containing it to or in said site.

8. Method according to claim 1, wherein said plant is constituted by a native vegetation cover pre-existing at said site.

9. Method according to claim 1 wherein said plant is a fast-growing tree.

10. Method according to claim 9, wherein said tree is a poplar.

11. Method according to claim 1, wherein said plant is an aquatic plant.

12. Method according to claim 11, wherein said plant is water reed.

13. Method according to claim 1, wherein said plant is an annual or biannual plant.

14. Method according to claim 13, wherein said plant is selected from the group consisting of clover, ryegrass, *Arabidopsis thaliana*, and the plants of the crucifer family (*Brassicaceae*).

15. Method according to claim 1, wherein said monosaccharide or disaccharide is introduced to said plant in an amount of 50 to 500 grams of monosaccharide or disaccharide per square meter of surface to be treated.

16. Method for phytoremediation of a site polluted by at least atrazine, which method comprising:

at least one step comprising cultivating, on said polluted site, at least one phytoremediation plant that absorbs said atrazine, wherein said step of cultivating is performed in the presence of at least one water-soluble exogenous monosaccharide or disaccharide which is absorbable by said plant or a substance containing such a monosaccharide or disaccharide wherein the monosaccharide or disaccharide protects cells in the plant from the effects of the atrazine and the effects of a superoxide ion produced within the plant by the introduction of atrazine, instead of blocking the action of the atrazine and the superoxide ion within the plant; and a subsequent step comprising collecting or destroying said plant that has absorbed said atrazine.

* * * * *